July 1, 1969 H. A. JOHNSON, JR., ET AL Plant Pat. 2,897
STRAWBERRY PLANT
Filed July 10, 1967
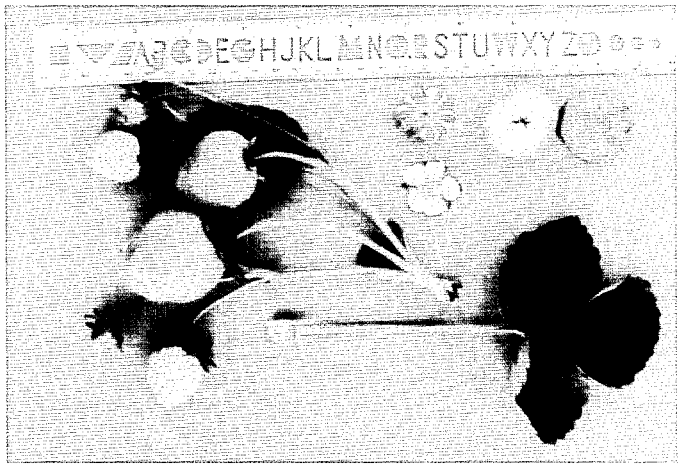
INVENTORS:
HAROLD A. JOHNSON, JR.
HAROLD E. THOMAS
BY
Townsend and Townsend
ATTORNEYS United States Patent Office Plant Pat. 2,897
Patented July 1, 1969

2,897
STRAWBERRY PLANT

Harold A. Johnson, Jr., and Harold E. Thomas, Morgan Hill, Calif., assignors to Driscoll Strawberry Associates, Morgan Hill, Calif., a corporation of California Filed July 10, 1967, Ser. No. 652,376
Int. Cl. A01h 5/08
U.S. Pit.—49 1 Claim This invention relates to a new and distinct variety of strawberry plant which is the result of a cross of the unpatented everbearing variety known as The Strawberry Institute of California selection No. E101.10 with the subject of United States Plant Patent No. 1,735, Goldsmith et al., issued July 29, 1958.

The seedlings resulting from the aforementioned cross were grown and asexually multiplied in Tehama County, Calif.; and tested in the fruiting beds of the Strawberry Institute's selection and testing grounds at San Martin, Calif. Clones of these seedlings were also held at The Strawberry Institute's Propagation Nursery in Shasta County. One plant was selected from the aforementioned group of seedlings, and further asexual reproduction was performed in the Shasta County nursery of the institute. Tests followed in various parts of California during intervening seasons on various institute members' properties. These tests indicated the merit of this new plant and resulted in its selection as a promising test variety.

A plant of the new variety, typical in size, shape and color, is pictured in the accompanying drawing in which two ripe berries are shown indicating some of the variations in shape found in this variety. A third berry of the plant is shown in cross section to exemplify flesh color and core cavity. The inflorescence pictured is typical of branching and relative size about the early part of July during which period the leaf shown is also typical in appearance and size. The flower, petals, and calyx shown are from secondary flowers.

A distinguishing characteristic of this everbearing plant is that it may be planted during spring months as well as during the winter and a crop can be realized in this same growing year. Also, the plant is vigorous for an everbearer, and medium to large berries can be harvested continuously from late spring through early fall in large amounts. The foliage of this new invention is distinct in that it is light in color and the leaflet margins are cupped upward. The fruit is also considered light in color as compared to the Goldsmith variety. The plant is a poor runner maker at the nursery with a lower increase rate than that of Goldsmith or the Institute E2. (The Institute E2 is the everbearing variety of United States Patent No. 2,611.)

Another group of characteristics distinguishing this new variety resides in the various features of its fruit and cropping pattern. The fruit size coming from the crown crop, which is the crop that is initiated while the plant is still at the nursery, is not as large as the E2 and the fruit size of the subsequent main crop does not reach E2 in size. This main crop does come heavier however, with more consistent cropping and more inflorescence per plant than the E2. The fruit shape is more globose than E2 or Goldsmith and the fruit gives a rounder appearance in the shipping crate. The fruit color is lighter than E2 or Goldsmith. The fruit is more often obscured by the foliage even though flowers may be visible above the foliage. The flesh is also lighter in color than Goldsmith and has a smaller core cavity. The fruit surface is usually smoother than E2 or Goldsmith, but during some periods in the fruiting season the fruit apex may become folded and seedy distracting from its normal appearance. The inflorescence is usually shorter than the Goldsmith, but the pedicels holding the primary berries originate from the axil formed from the union of two or three peduncles, as is the common occurrence with Goldsmith.

The flowers produce anthers with abundant visible pollen allowing this variety to produce well formed fruit under cold, windy wet conditions. The single leaflet bract that originates from the axil mentioned above is often noticeably large (see drawing photograph).

This new plant does not generally grow as large as Goldsmith, neither do the leaves become as large, but it may become denser. If the plant is held for fruiting two years, the plant may produce many crowns which tend to produce a dense plant; this is especially true if the plant is given high amounts of nitrogen fertilizer. The leaflets are distinct in that they are lighter in color, the margins are cupped upward and the surface is less rugose than the Goldsmith. The calyx diameter is smaller with narrower shaped sepals as compared to Goldsmith. The sepals are similar to Goldsmith in that there are only a few serrations at the apex.

The dessert quality of this variety is superior in comparison to the Goldsmith and has a mild sub-acid flavor. There is generally no particular aroma peculiar to the flesh of this new variety.

The new variety of this invention is susceptible to verticillium wilt, red stele disease, and powdery mildew, but has a higher level of tolerance to two-spotted mite than does E2. As a seedling this variety withstood the natural virus invasion of the virus components found in the Santa Clara Valley without losing its ability to produce.

The varietal characteristics of this new plant described in detail were observed during the first fruiting year. Observations were made in Salinas, Watsonville and Pescadero areas of California which are cool coastal areas near the Pacific Ocean. The color terminology is in accordance with Ridgeways Color Standards and Nomenclature (1912 edition).

*Plant.*—Medium size, open, but may become dense with high nutrient levels. Extensive root system.

*Leaves.*—Medium size and abundant, central leaflet mostly 5 to 8 cm. in diameter with the width mostly equalling the length. Petioles and leaflets light in color and leaflets are smooth becoming only slightly rugose, margins are consistently cupped upward. Serrations of leaflet margins are ovate with an acute apex, many with a double point. Bracts may be present on the petioles. Leaflet upperside color at Watsonville during July is Forest Green, Plate XVII.

*Inflorescence.*—Abundant, medium length, mostly 16 to 22 cm. during July. The pedicel holding the primary berry usually originates at the axil formed by the union of two or three peduncles (see drawing photograph). In some cases the pedicel holding the primary berry originates from one of the peduncles. Most hair on the tertiary pedicel 20 mm. below the flower usually lays against and parallel to the pedicel. Flowers may be visible above the foliage and produce abundant pollen.

*Fruit.*—Medium size; primary berries are mostly 40 mm. in length and 40 mm. in width and may drop some in size during the season. In outline the fruit is mostly globose conic to globose wedge as described in U.S.D.A. Bulletin No. 1043. Fruit surface is generally smooth with a medium gloss; apex may become slightly folded and seedy at times. The shoulders of most berries are large and round, not necked. The skin and flesh are firm and the core cavity is considered small. The surface fruit color is Scarlet Red, Plate I. The flesh perimeter color is Scarlet, Plate I, and the core color is Orange Pink, Plate II.

*Seeds.*—The seeds are abundant, of medium size, and very few are non-fertile. The seed may be held slightly below to equal with the surface. The seed color is Wax Yellow, Plate XVI, becoming dark when exposed to full sunlight.

*Calyx.*—The calyx is small, mostly 32 to 36 mm. in diameter and usually joins the pedicel at a point sunken within the fruit outline if the berry is viewed from the side, giving the calyx a slightly reflexed appearance. The calyx is capped with difficulty except when fully ripe. The sepals are not large and serrations are scarce on secondary and tertiary fruit. The color of the sepals on the side facing the fruit is mostly Spinach Green, Plate V.

We claim:

1. The new and distinct variety of strawberry plant herein described and illustrated, and identified by the characteristics enumerated above.

No references cited.

ROBERT E. BAGWILL, *Primary Examiner.*